United States Patent
Ibsen et al.

[11] Patent Number: 5,876,743
[45] Date of Patent: Mar. 2, 1999

[54] BIOCOMPATIBLE ADHESION IN TISSUE REPAIR

[75] Inventors: Robert L. Ibsen, Santa Maria; William R. Glace, Orcutt, both of Calif.

[73] Assignee: Den-Mat Corporation, Santa Maria, Calif.

[21] Appl. No.: 934,570

[22] Filed: Sep. 22, 1997

Related U.S. Application Data

[63] Continuation of Ser. No. 668,595, Jun. 18, 1996, abandoned, which is a continuation of Ser. No. 408,013, Mar. 21, 1995, abandoned.

[51] Int. Cl.$^6$ .................................................. A61F 2/28
[52] U.S. Cl. ........................................ 424/426; 523/115
[58] Field of Search ............................ 523/115; 424/426

[56] References Cited

U.S. PATENT DOCUMENTS

| | | | |
|---|---|---|---|
| Re. 33,100 | 10/1989 | Ibsen et al. | 106/35 |
| Re. 34,937 | 5/1995 | Ibsen et al. | 106/35 |
| 3,566,874 | 3/1971 | Shepherd et al. | 128/349 |
| 3,632,416 | 1/1972 | Shepherd et al. | 117/135.5 |
| 3,674,901 | 7/1972 | Shepherd et al. | 424/27 |
| 3,849,185 | 11/1974 | Shepherd et al. | 117/161 |
| 3,860,490 | 1/1975 | Guttag | 195/108 |
| 3,868,447 | 2/1975 | Kliment | 424/81 |
| 3,941,858 | 3/1976 | Shepherd et al. | 260/885 |
| 4,081,402 | 3/1978 | Levy et al. | 252/428 |
| 4,303,066 | 12/1981 | D'Andrea | 128/456 |
| 4,674,980 | 6/1987 | Ibsen et al. | 433/228.1 |
| 4,738,722 | 4/1988 | Ibsen et al. | 106/35 |
| 4,964,911 | 10/1990 | Ibsen et al. | 106/35 |
| 5,112,640 | 5/1992 | Warunek et al. | 427/2 |
| 5,151,453 | 9/1992 | Ibsen et al. | 522/14 |
| 5,292,515 | 3/1994 | Moro et al. | 424/422 |
| 5,334,625 | 8/1994 | Ibsen et al. | 523/115 |
| 5,360,770 | 11/1994 | Chadwick | 501/24 |
| 5,401,783 | 3/1995 | Bowen | 523/116 |

OTHER PUBLICATIONS

Scherer et al., "New Subgingival Restorative Procedures With Geristore® Resin Ionomer," Practical Periodontics And Aesthetic Dentistry Supplement, Jan./Feb. 1995, 6 pages.

Insert, "Geristore Fluoride–Releasing Restorative", printed by Den–Mat Corporation Jan. 1994, 1 sheet.

Insert, "Instroducing, Geristore Multi–Shade Kit" printed by Den–Mat Corporation Mar. 1994, 1 sheet.

Insert, "Geristore Solutions, Geristore Bonding Restorative," printed by Den–Mat Corporation, Nov. 1991, 1 sheet.

(List continued on next page.)

*Primary Examiner*—Carlos A. Azpuru

[57] ABSTRACT

A process for enhancing the
(a) normal healing processes involving a live mammalian body of
  (i) injured non-dental-related soft tissue, and
  (ii) non-dental-related osseous material, and
(b) for enhancing the biocompatibility and adhesion of bone and/or prosthetic device involved in a non-dental surgical or nonsurgical repair procedure, to ossified and non-ossified tissue components with which they are in contact, where there is an injury to either soft or hard tissue or a non-biocompatible prosthesis is placed in the body, that involves placing at the injury or on the prosthesis
  a) a primary coating that is a tenaciously-bonded hydrophilic water insoluble crosslinked resin coating,
  b) that optionally contains a measurable amount of a water/fluid leachable fluoride capable of (a) being leached from the coating in a metered amount, and (b) transporting a small amount of leached fluoride from the coating into the afflicted area ("the primary coating with fluoride").

51 Claims, 3 Drawing Sheets

OTHER PUBLICATIONS

Insert, "Tenure Solutions, Tenure All Surface Bonding System," printed by Den–Mat Corporation Mar. 1193, 1 sheet.

Instruction Sheet, Tenure® All–Surface Bonding System, printed by Den–Mat Corporation Sep. 1993, 1 sheet.

Insert, Tenure®, 1995, 1 sheet.

Hydrone® Wounded Dressing brochure, 1986, Acme/Chaston, Dayville, CT 06241, 10 pages.

Galan, D., "Clinical Application of Geristore Glass–Ionomer Restorative in Older Dentitions," Journal of Esthetic Dentistry, vol. 3, No. 6, Nov.–Dec. 1991, pp. 221–226.

Pacropis, et al., Current Geristore® Research, "Studies On A Fluoride Releasing Adhesive To Various Substrates" Abstract #1703, Int'l. Assoc. for Dental Research/American Association for Dental Research, 1991 Gen. Session, Acapulco, Mexico, 1 sheet.

The Dental Advisor, "Temporization," vol. 9, No. 1, Mar. 1992, 8 pages.

Wieczkowski, et al., "Microleakage Evaluation In Amalgam Restorations Used With Bases," Journal of Esthetic Dentistry, vol. 4, No. 2, Mar./Apr. 1992, pp. 37–40.

Clinical Research Associates Newsletter, Subject; Glass Ionomer–Resin—State–Of–Art vol. 17, Issue 3, Mar. 1993, 4 pages.

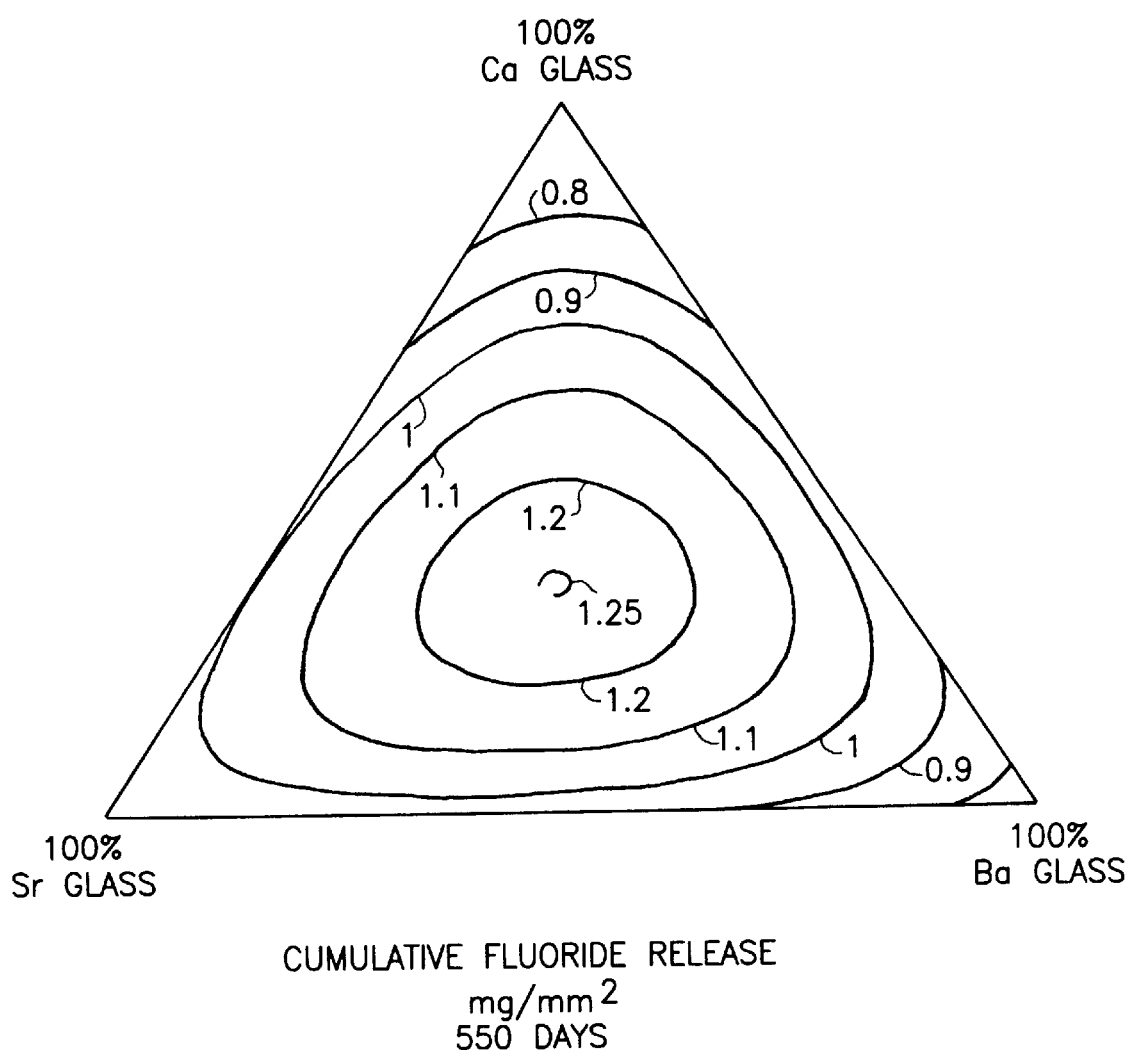

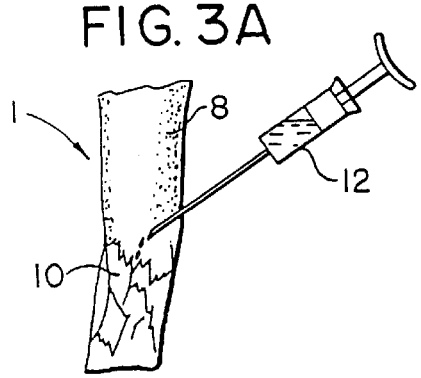
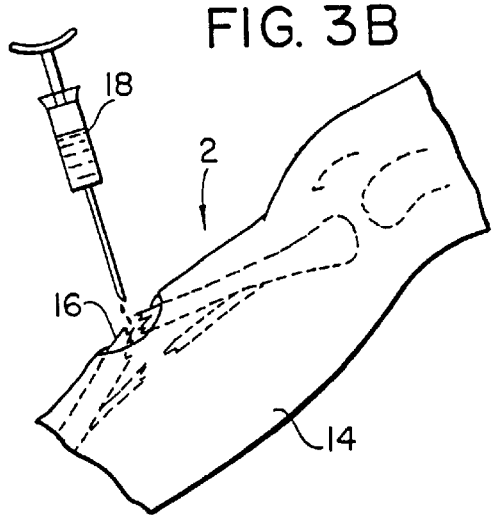
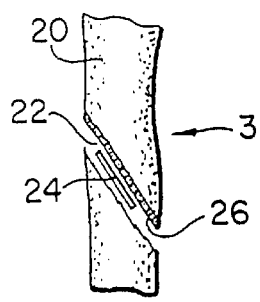
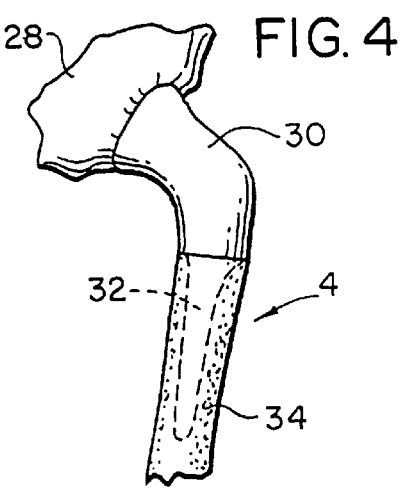
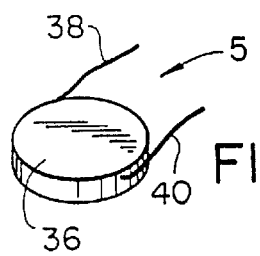
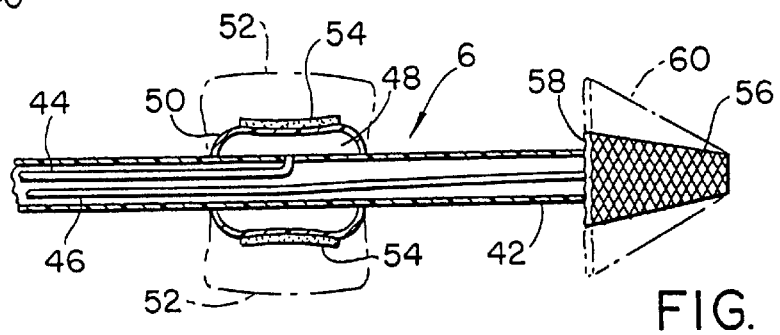

BIOCOMPATIBLE ADHESION IN TISSUE REPAIR

This application is a continuation of application Ser. No. 08/668,595 filed Jun. 18, 1996, now abandoned, which is a continuation of application Ser. No. 08/408,013, filed Mar. 21, 1995, now abandoned.

BRIEF DESCRIPTION OF THE INVENTION

The invention relates to a process for aiding tissue repair in non-dental treatment of a mammal that involves the (a) healing process of (i) injured soft tissue, and (ii) damaged osseous material, and (b) for enhancing the biocompatibility and adhesion of bone and/or prosthetic device (typically made of metal, ceramic or plastic) involved in a surgical or nonsurgical repair procedure, to ossified and non-ossified tissue components with which they are in contact. The invention involves treating the injured non-dental related soft tissue, osseous material, bone and/or prosthetic device with a special biocompatible crosslinked resin that optionally contains leachable fluoride.

BACKGROUND OF THE INVENTION

Dentistry is the science concerned with the diagnosis, prevention, and treatment of diseases of the teeth, gums, and related structures of the mouth and includes the repair or replacement of defective teeth. Dental (i.e., relating to, or for the teeth) treatments involve those compositions, articles and processes encompassed within the field of dentistry. The terms "non-dental applications and treatments" and "non-dental-related", as used herein and in the claims hereof, address activities exclusive of activities that are part of the field of dentistry.

Geristore™ and Tenure™, sold by Den-Mat Corporation, Santa Maria, Calif., are promoted for certain uses in dentistry. U.S. Pat. Nos. 4,738,722, 5,334,625 and 5,151,453, incorporated herein by reference, describe Geristore™. Geristore™ is a small particle composite that contains fluoride, is radiopaque and hydrophilic. It has low-cure shrinkage, low coefficient of thermal expansion and high strength. It aggressively bonds by chemical coupling to dentin, enamel, composites used in dentistry, porcelain and metal, such as stainless steel. It is a paste/paste formulation that is easy to mix. It is capable of rapid cure by exposure to room temperature and for more rapid cure, by exposure to light. In addition, though it contains a fluoride, which could be toxic when ingested in large dosages, it is biocompatible and safe to use within a human or other animal when applied topically.

Tenure™ is a solvent based crosslinkable acrylic resin, provided as a solution/solution formulation. Its composition is described in U.S. Pat. No. 4,964,911, patented Oct. 27, 1990, and more effectively disclosed in allowed copending application Ser. No. 965,102, filed Oct. 22, 1992, to issue as U.S. Pat. Re 34,937, the disclosure of which is incorporated by reference. It is not an ionomer and does not release fluoride ion. It is less hydrophilic than Geristore™. It too is a crosslinkable resin. It contains a volatile solvent (typically acetone), which readily evaporates. After evaporation, a film of the resin rapidly cures in situ. Tenure™ bonds by chemical coupling to dentin, enamel, porcelain, metal and the composites typically used in dentistry. It has been recommended for use with Geristore™ in chemically bonding Geristore™ to dentin or enamel.

Galan, *Journal Of Esthetic Dentistry*, Vol. 3, No. 6, (Nov./Dec. 1991), describes the general use of Geristore™ in the restoration of teeth and lesions both supra and subgingivally located.

M. Dragoo (unpublished) has used Geristore™ in subgingival restorations of teeth to treat subgingival root resorption, split roots, endo perforation, tooth fracture, external root resorption and root coverage over previously restored and/or eroded root surfaces. He found the Geristore™ aided in rebuilding biologic width, resulting in new tissue attachment, and minimized plaque induced gingivitis.

There is much art on the use of hydroxyethylmethacrylate ("HEMA") to make hygroscopic polymers such as a homopolymer of HEMA ("PHEMA"). Such HEMA based polymers typically form water swellable hydrogels. HEMA contains the sym. (or 1,2-) ethylene bis-methacrylate (ethylene glycol dimethacrylate) as a byproduct. This byproduct crosslinks the HEMA based polymers to allow formation of useful hydrogels. One such hydrogel form is used to make soft contact lens by cast molding HEMA containing small amounts of ethylene bis-methacrylate. One advantage of PHEMA based systems that allows use in physiological applications is the biocompatibility of the polymer. However, their use as described in the patent literature has been limited merely to transporting drugs and other materials to a bodily function based on their absorptive qualities or as an inert interface about a device to render that device biocompatible. See for example, U.S. Pat. No. 3,566,874, which describes the encapsulation of a catheter with a casting syrup of HEMA. The hydrogel form of the polymer of HEMA ("PHEMA") is renowned for its capacity to absorb moisture to generate a swollen film. Some patents describe PHEMA products into which other ingredients have been absorbed. In this respect, the PHEMA product, as such, is merely a reservoir for that ingredient. U.S. Pat. No. 3,566,874 describes the inclusion in a HEMA casting syrup of a germicide or an antibiotic. U.S. Pat. No. 4,303,066, makes a burn dressing by dispensing separate phases of a PHEMA and a high boiling liquid on a burn to serve as a dressing. As a consequence, the absorptive characteristic of PHEMA is being used only for the high boiling liquid which is provided supposedly for heat transfer purposes. U.S. Pat. No. 3,674,901 describes the coating of a HEMA based solvent solution to coat surgical suture threads. The patent includes antibiotics, antiseptics or bactericides absorbed into the cured resin. In this case, however, the resin is foamed first before the adsorption takes place. In U.S. Pat. No. 3,849,185, a HEMA coumarone-indene type resin casting material is mixed with materials such as heparin and used as a coating material. On the other hand, U.S. Pat. No. 3,868,447 describes a highly filled solvent-based HEMA paste to which biologically active ingredients can be added. The paste has been described for use in dental applications, such as a cover for dental fillings, or as a carrier for Novocain™ in dental surgery.

Though HEMA and PHEMA contain hydroxyl groups and hydroxyl groups are thought to aid in adhesion, the adhesion of such groups to a physiologically active surface is materially and adversely affected by the presence of water at the surface. Consequently, bonding of HEMA to a physiologically involved surface which contains moisture at its surface requires some ingredient in the resin that aids in bonding to such a surface.

THE INVENTION

Non-dental related body tissues are oftentimes subjected to undesirable afflictions such as irritation, decay or damage of bone or soft tissue. Irritation can be reflected in inflammation, decay can involve erosion and/or decomposition of tissue, and damage can be a wound or fracture. This invention involves topically treating mammalian, preferably human and domestic animal, non-dental-related, afflicted tissue with certain coating materials to decrease the impact of such afflictions.

More particularly, the invention relates to a process for enhancing the (a) normal healing process of
  (i) injured non-dental-related soft tissue, and
  (ii) non-dental-related osseous material, and
(b) for enhancing the biocompatibility and adhesion of bone and/or prosthetic device (typically made of metal, ceramic or plastic) involved in a non-dental surgical or nonsurgical repair procedure, to ossified and non-ossified tissue components with which they are in contact.

The invention relates to processes to enhance non-dental-related physiological functioning of a live mammalian body, preferably a live human or domesticated animal body, where there is an injury to either soft or hard tissue or a non-biocompatible prosthesis is placed in the body, that involves placing at the injury or on the prosthesis a) a tenaciously-bonded hydrophilic water insoluble crosslinked resin coating (hereinafter called "the primary coating")

b) that optionally contains a measurable amount of a water/fluid leachable fluoride capable of (a) being leached from the coating in a metered amount, and (b) transporting a small amount of leached fluoride from the coating into the afflicted area (hereinafter called "the primary coating with fluoride").

In one aspect, the invention encompasses a process for enhancing the normal healing processes of a non-dental related wound, and the biocompatibility and adhesion of non-dental-related bone and/or prosthetic device (typically made of metal, ceramic or plastic) involved in a non-dental-related surgical and/or wound repair procedure, to body cellular (e.g., tissue) components with which they are in contact. This is accomplished by providing during such procedure, at the area of a wound, a surface containing the primary coating or the primary coating with fluoride. The amount of fluoride provided in the primary coating is insufficient to cause fluorosis or any other toxic reaction, and, by processes unknown, except possibly antimicrobial processes, the fluoride assists the normal processes of wound healing. The invention also relates to a process for joining bone and/or prosthetic device surfaces in non-dental-related surgical procedure, by applying the primary coating or the primary coating with fluoride, to tenaciously bond to one or more of the surfaces prior to completion of the surgical repair.

The invention also encompasses in these non-dental-related processes, the use of a composite layering of a strongly adhesively-bonded crosslinkable acrylic resin, possessing less hydrophilicity than the primary coating with or without fluoride, that rapidly in situ cures on an application surface, the bone and/or prosthetic surface, to function as a primer (hereinafter called the "primer coating") for the primary coating with or without fluoride that is applied to the same surface(s). The biocompatibility of the primary coating on the surface, bone and/or prosthetic device over the primer coating enhances healing, the adhesion of the bone to bone and bone to softer tissue, and prosthetic device to bone or softer tissue, and precludes or minimizes bone or softer tissue rejection to the surgical procedure.

More particularly, the invention relates to a non-dental-related topical wound treatment that involves the application over a wound of a film or layer of the primary coating with or without fluoride. The primary coating with or without fluoride may be cured as a thin film on a non-adhesive surface such as glass or Teflon® and as a released film may be put in contact with the wound. The primary coating with or without fluoride may be coated on an adhesive receptive surface (such as plastic or cloth) and cured, and then applied to the wound in the manner of a wound dressing. The primary coating is stable on contact with the wound, and promotes healing of the wound. This allows fluid contact with the optionally provided fluoride component within the coating and, by virtue of the releasibility of the fluoride by leaching, fluoride is metered from the coating and into the wound area. Because of the nature of the source of fluoride, it is possible to control the leaching rate of fluoride and obtain a predetermined metered amount of fluoride transported from the coating into the wound area.

Also, the invention relates to a process for enhancing the biocompatibility and adhesion of bone and/or prosthetic device (typically made of metal, ceramic or plastic) during a non-dental-related surgical procedure, to soft tissue with which they are in contact. This is accomplished by joining non-dentalrelated bone and/or prosthetic device surfaces after applying the primary coating with or without fluoride to one or more of the surfaces prior to completion of the repair. It is also desirable to utilize a composite layering of the primer coating and the primary coating with or without fluoride. In this embodiment, the primer coating rapidly in situ cures (e.g., cold cures or autopolymerizes) on the bone and/or prosthetic surface before primary coating is applied to that same surface(s). The biocompatibility of the primer coating on the bone and/or prosthetic device enhances the adhesion of the bone to bone and bone to tissue, and prosthetic device to bone or tissue, while at the same time averting or minimizing bone or tissue rejection to the surgical procedure.

This invention is directed to a novel non-dental-related process in which primary coating with or without fluoride alone, or in combination with the primer coating, is topically applied to non-dental-related bone, prosthesis and soft tissue to enhance the biocompatibility and adhesion of bones and/or prosthetic devices involved in body repair. The enhancement of biocompatibility is believed to occur due to the inherent biological compatibility of the coating, its safe and substantial bonding to bone or a medical device implanted in the body, and, when present, through the metered release of small and safe quantities of fluoride to thereby aid the healing process. It is believed that the fluoride provides in the wound safe antimicrobial properties, thereby advancing the healing process.

In a further particular embodiment of the invention, in a non-dentalrelated surgical procedure involving bone repair within a body, such as a bone fracture, which involves the process of incising skin to expose an area in which bone undergoing restoration resides, exposing the bone undergoing repair, defining within the exposed area the manner of restoration of the bone, preparing the area for said restoration, effecting the restoration, and closing the area after completion of the surgical procedure by closing the skin over the area and providing for the natural or aided healing of any wound associated with such procedure, the improvement which comprises, during said restoration, the step of selecting at least one bone surface within the exposed area that is to be bonded, coating that surface with the primary coating with or without fluoride, alone or in combination, such as in sequence, with the primer coating, contacting the coated surface with bone or a prosthetic device, curing the coating by exposing the coating to light or to ambient temperature.

In still another particular embodiment of the invention, in a non-dentalrelated surgical procedure to implant a prosthetic device within a body which involves the process of incising skin to expose an area of the body in which the prosthetic device is to be inserted, defining within the exposed area the manner of restoration therein by implantation of the prosthetic device, preparing the area for said restoration, effecting the restoration, and closing the area after completion of the surgical procedure by closing the skin over the area and providing for the natural or aided healing of any wound associated with such procedure, the improvement which comprises, during said restoration, the step of selecting at least one prosthetic device surface within the exposed area that is to be bonded, coating that surface with the primary coating with or without fluoride alone, or in combination, such as in sequence, with the primer coating, contacting the coated surface with bone and/or tissue, or including the step of adding a patch of cured film of the primary coating with fluoride, curing the coating by exposing the coating to light or to ambient temperature.

In an another embodiment of the invention, there is described a nondental-related process for aiding in the healing of an open wound or an exposed wound (such as a subcutaneous, penetrating (including a traumatopneic wound), perforating, or tangential wound) which comprises superimposing a cured layer of primary coating with fluoride onto the wound such that the tissues at the wound surface are in direct contact with the layer, and maintaining such a layer in contact with the wound at least until such time as the wound is closed as a result of the healing process. In this treatment, it is desirable to form a thin cured layer of primary coating with fluoride, coat one surface of the cured layer with uncured primary coating with fluoride, and cure the coating while it and the cured layer are in contact with the wound by exposing the uncured coating to light or to ambient temperature.

In still another embodiment of the invention, there is described a nondental-related process for repairing an injured or degenerated osseous material which comprises superimposing a patch of cured layer of the primer coating with fluoride onto the injured or degenerated area of the osseous material, leaving such patch in contact with the area and allowing growth of the osseous material to encompass the patch and repair the injured or degenerated area. In this treatment, it is desirable to form a thin layer primary coating with fluoride, and coat one surface of the cured layer with uncured primary coating with fluoride, and cure the primary coating while it and the cured layer is in contact with the area undergoing treatment by exposing the coating to light or to ambient temperature.

The primary coating comprises a resin based on an ethylenically unsaturated-functional monomer that contains a hygroscopic group. The ethylenically-unsaturated-functional monomer contains hygroscopic groups and exhibits hydrophilicity. Typical of such groups are hydroxyl, amide, amine, aliphatic ether, amine, hydroxyalkyl amine, hydroxyalkyl amide, pyrrolidone, ureyl, and the like.

Another ingredient of the primary coating composition is a polycarboxylic acid, i.e., a polymer that contains pendant carboxyl groups. The polycarboxylic acid is thought to enhance bonding of the primary coating resins to metallic and other substrates, particularly to organic and inorganic salt forming materials that are present in the substrate to which the primary coating is applied. In addition, the polycarboxylic acid enhances the bonding of the resin components of the primary coating composition to any inorganic fillers provided in the coating formulation. In a number of contemplated uses for the primary coating, in accordance with this invention, the polycarboxylic acid may be excluded from the primary coating formulation. In addition, one may employ the alkali metal salt of the polycarboxylic acid.

In addition, the primary coating contains a variety of crosslinking agents. One type of crosslinking agent is "hard crosslinker" and another is a "soft crosslinker." Both hard and soft crosslinker are polyfunctional molecules in which the functionality is complementary to the ethylenic unsaturation of the ethylenically-unsaturated-functional monomer. In the case of the hard crosslinker, the functional groups are bonded via an aliphatic group of up to carbon atoms, to a central moiety that is aromatic in nature, that is, comprises a group that has the rigidity characteristics of a benzene ring. Illustrative of such rigid groups are aromatic rings such as benzene, biphenyl, anthracyl, benzophenone, norbornyl, and the like. Such hard crosslinkers raise the $T_g$ of the cured coating.

The soft crosslinker contains the functional groups bonded to a central moiety that is aliphatic in nature, that is, comprises a group that has the flexibility of an alkane or an alkyl benzene containing. Illustrative of such flexible groups are the residues of ethylene glycol, diethylene glycol, 2,2-bis(4-hydroxyphenyl)propane, 2,2,-bis(4-hydroxyphenyl) fluorinated alkanes, and the like. Such soft crosslinkers toughen the cured coating and can raise the $T_g$ of the cured coating, but not as high as the typical hard crosslinker.

Another feature of the primary coating is that it tenaciously bonds to surfaces onto which it is coated as well as securely tie up any inorganic filler that is included in the primary coating formulation. In order to achieve this, the coating contains a coupling agent as part of its formulation. These coupling agents provide chemical bonding to the surface to which the coating is applied. Chemical bonding means strong and weak bonding forces. Strong bonding forces, as used herein, refers to covalent, ionic, hydrogen bonding and complexation, and weak bonding forces, encompasses the other forms of bonding. Where weak bonding forces are employed, the extent of such bonding is such that the adhesion to the surface is of the nature of a stronger bonding force. For example, van der Waal forces are weak bonding forces. In the case of the invention, the amount of such forces existing between the coating and the surface will be sufficient to give the performance of a stronger bonding force.

A desirable coupling agent is a material, such as a molecule, that is functionally complementary to the ethylenically-unsaturated-functional monomer. Desirably, the coupling agent contains a functional group that is reactable with the ethylenic unsaturation. Preferably, the functional group is an acrylic-type ethylenic unsaturation. At another part of the coupling agent molecule is a surface bonding group that can impart one or more properties to the primary coating:

1) chemical bonding capabilities to the substrate surface to which the primary coating is applied; and/or 2) wetting agent properties in that it reduces the surface tension of the coating, causing the coating to spread across or penetrate more easily the surface of the substrate onto which the primary coating is applied.

The utilization the primary coating with fluoride is a special and significant embodiment of the invention. The fluoride component optionally provided in the primary coating is desirably present in the coating such that it is leachable from the coating over an extended period of time.

In order to cure the primary coating, the primary coating formulation is provided with a conventional free-radical catalytic curing agent and/or a freeradical photoinitiator. When both are provided, the coating can be cured by each of the system, preferably by both to insure that volatile monomeric components are left as residual components in the coating. This avoids the possibility of toxic reaction to the presence of such volatile monomeric components.

In respect to the above processes, the invention relates to the improvement where the primary coating comprises a two component system of:

(a) a first component comprising:
(1) the fluoride source, such as a particulate siliceous fluoride containing filler in which the fluoride is water leachable;
(2) a coupling agent, such as one or more of (i) N-phenylglycine, the alkali metal salt thereof, or the mixture of the foregoing two compounds, (ii) the adduct of N-(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds;
(3) a photoinitiator; if desired, a radiopaquing agent; and, if desired, a buffering agent; and (b) a second component comprising:
(1) the ethylenically-unsaturated-functional monomer;
(2) a soft crosslinker such as 2,2-bis(4-methacryloxy 2-ethoxy phenyl)propane, diethyleneglycol bis methacrylate, and the like;
(3) a hard crosslinker such as one or more of (i) the adduct of pyromellitic acid dianhydride and 2-hydroxyethyl methacrylate, (ii) the adduct of 3,3', 4,4'-benzophenonetetracarboxylic dianhydride and 2-hydroxyethylmethacrylate, (iii) 4-methacryloxyethyltrimellitic anhydride, and (iv) other compounds containing at least one group or moiety capable of free radical polymerization and at least one aromatic ring or moiety containing electron-withdrawing substituents that do not interfere with free radical polymerization;
(4) a photoinitiator;
(5) a polymerized carboxylic acid;
(6) a free-radical scavenger; and
(7) a curing catalyst.

In another embodiment of the primary coating, it may be a light-curable adhesive composition of the following two-component system:

(a) a first component comprising:
(1) a fluoride source such as a particulate siliceous fluoride containing filler in which the fluoride is water leachable;
(2) a soft crosslinker;
(3) an ethylenically-unsaturated-functional monomer;
(4) a photoinitiator;
(5) a free-radical scavenger;
(6) a thermal initiator;
7) a polymerized carboxylic acid;
(8) a hard crosslinker such as one or more of (i) the adduct of pyromellitic acid dianhydride and 2-hydroxyethyl methacrylate; (ii) the adduct of 3,3', 4,4'-benzophenonetetracarboxylic dianhydride and 2-hydroxyethylmethacrylate, (iii) 4-methacryloxyethyltrimellitic anhydride, and (iv) other compounds containing at least one group or moiety capable of free radical polymerization and at least one aromatic ring or moiety containing electron-withdrawing substituents that do not interfere with free radical polymerization, and (b) a second component comprising:
(1) a fluoride source such as a particulate siliceous fluoride containing filler in which the fluoride is water leachable;
(2) a soft crosslinker;
(3) an ethylenically-unsaturated-functional monomer;
(4) a coupling agent such as one or more of (i) N-phenylglycine, the alkali metal salt thereof, or the mixture of the foregoing two compounds, (ii) the adduct of N-(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds;
(5) a photoinitiator; if desired, a radiopaquing agent; and, if desired, a buffering agent.

A more specific embodiment of the primary coating composition is the following composition:

1. A particulate glass having the composition set forth in Table 1 below;
2. A coupling agent:
The alkali metal salt of the adduct of N-(p-tolyl)glycine and glycidyl methacrylate; e.g.,

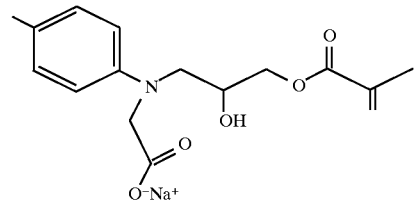

1. A hard crosslinker: The adduct of pyromellitic acid dianhydride and 2-hydroxyethyl methacrylate;
2. A photoinitiator: Ethyl 4-dimethylamino benzoate and camphoquinone (i.e., 2,3-bornanedione);
3. A soft crosslinker: Ethoxylated bisphenol A dimethacrylate and the adduct of glycidylmethacrylate and bisphenol A,
4. An ethylenically-unsaturated-functional monomer: 2-hydroxyethyl methacrylate;
5. Butylated hydroxytoluene free radical scavenger.
6. A polycarboxylic acid;
7. Benzoyl peroxide or other peroxides that cause free radical addition at about 55° C. or at a lower temperature.

The primer coating involves a two part (package) composition, comprising (a) a compound selected from the group consisting of (1) N-phenylglycine, (2) the adduct of N-(p-tolyl) glycine and glycidyl methacrylate, (3) the addition reaction product of N-phenylglycine and glycidyl methacrylate, (4) N(p-tolyl) glycine, N-phenylalanine, sarkosine, N-lauroylsarkosine, glycine, N,N-dimethyl-glycine, 3-(N-phenyl) amino propionic acid, 3-(N-ptolyl) amino propionic acid, omega-amino fatty acids, N-substitutedomega-amino fatty acids, and the other amino acids; in which each member of the group of (1), (2), (3) and (4) that is present in the solution is an alkali metal salt form of that member, and (b) a composition comprising at least one monomer selected from the group consisting of (1) the addition reaction product of pyromellitic acid dianhydride and 2-hydroxyethyl methacrylate, (2) the addition reaction product of 3,3', 4,4'-benzophenonetetracarboxylic dianhydride and 2-hydroxyethyl methacrylate, (3) 4-methacryloxyethyltrimellitic anhydride, and (4) other compounds containing at least one group or moiety capable of free radical polymerization and at least one aromatic ring or moiety containing electron-withdrawing substituents that do not interfere with free radical polymerization.

The use of the primer coating composition involves, in one preferred embodiment the steps of (a) first contacting the surface with an aqueous solution comprising at least one strong acid or acidic salt in order to condition the surface, (b) then contacting the surface with a solution comprising a solvent and at least one compound selected from the group consisting of (1) N-phenylglycine, (2) the adduct of N-(p-tolyl)glycine and glycidyl methacrylate, (3) the addition reaction product of N-phenylglycine and glycidyl methacrylate, and (4) other amino acids, in which each member of the group of (1), (2), (3) and (4) that is present in the solution is an alkali metal salt form of that member, heat the surface to remove the solvent or maintain the surface at ambient temperature until the solvent is evaporated, and (c) then contacting the surface with a solution comprising at least one monomer selected from the group consisting of (1) the addition reaction product of pyromellitic acid dianhydride and 2-hydroxyethyl methacrylate, (2) the addition reaction product of 3,3', 4,4'-benzophenone tetracarboxylic dianhydride and 2-hydroxyethyl methacrylate, (3) 4-methacryloxyethyltrimellitic-anhydride, and (4) other compounds containing at least one group or moiety capable of free radical polymerization and at least one aromatic ring or moiety containing electron-withdrawing substituents that do not interfere with free radical polymerization (d) heat the surface to remove residual solvent or maintain the surface at ambient temperature until the solvent is evaporated from the primer coating and the coating is fully reacted.

In a further embodiment of the invention, there is described a healing aid comprising a thermoplastic resin containing the aforementioned water leachable fluoride. Preferable, the thermoplastic resin comprises a hydrophilic resin that is water insoluble and the fluoride source is the aforementioned inorganic fluoride containing compositions in which the fluoride is water leachable. The thermoplastic resin is a linear polymer that contains such groups as hydroxyl, carboxylic acid, amide, amine, aliphatic ether, amine, hydroxyalkyl amine, hydroxyalkyl amide, pyrrolidone, ureyl, and the like. A desirable linear polymer is one that comprises polymerized vinyl alcohol or polymerized HEMA or 2,3-dihydroxypropylacrylate as a significant component of the polymer. Also desirable are copolymers of vinyl alcohol and vinyl acetate, copolymers of vinyl alcohol and ethylene, copolymers of vinyl alcohol and acrylic acid, polyacrylic acid, and the like.

This invention includes placing a flexible coating or film of the hydrophilic thermoplastic polymer containing the leachable fluoride dispersed therein on an injured portion of a mammalian body, preferably a human or a domesticated animal, and allow fluoride to be released from the coating or film to contact and penetrate into the injured area. This technique can employ the film as a component of a bandage, much like a "Band-AidT™" to adhesively secure the cured film to the injury, and replacing the bandage periodically in order to optimize treatment of the injury. In the last embodiment, there is a wound dressing where the adhesive receptive surface comprises a pressure sensitive adhesive to form an adhesive bandage

BRIEF DESCRIPTION OF THE DRAWINGS

FIG. 2 is an area plot of concentration of a siliceous fluoride source from which one may obtain long term and uniform leaching of fluoride.

FIG. 3 is an illustrative rendering of bone fractures treated in accordance with this invention. FIG. 3A shows the treatment of a comminuted fracture, FIG. 3B shows the treatment of a compound fracture, and FIG. 3C involves the use of a patch of primary coating in a spiral bone fracture.

FIG. 4 is an illustrative rendering of hip prosthesis located in the hip joint and the femur to which the process of this invention is applied.

FIG. 5 is an illustrative rendering of a heart pacemaker to which is applied the primary coating.

FIG. 6 schematically illustrates catheter arrangements suitable for applying primary coating to vessel intima, and removing encrusted plaque from the vessel.

DETAILED DESCRIPTION OF THE INVENTION

Figure 1:
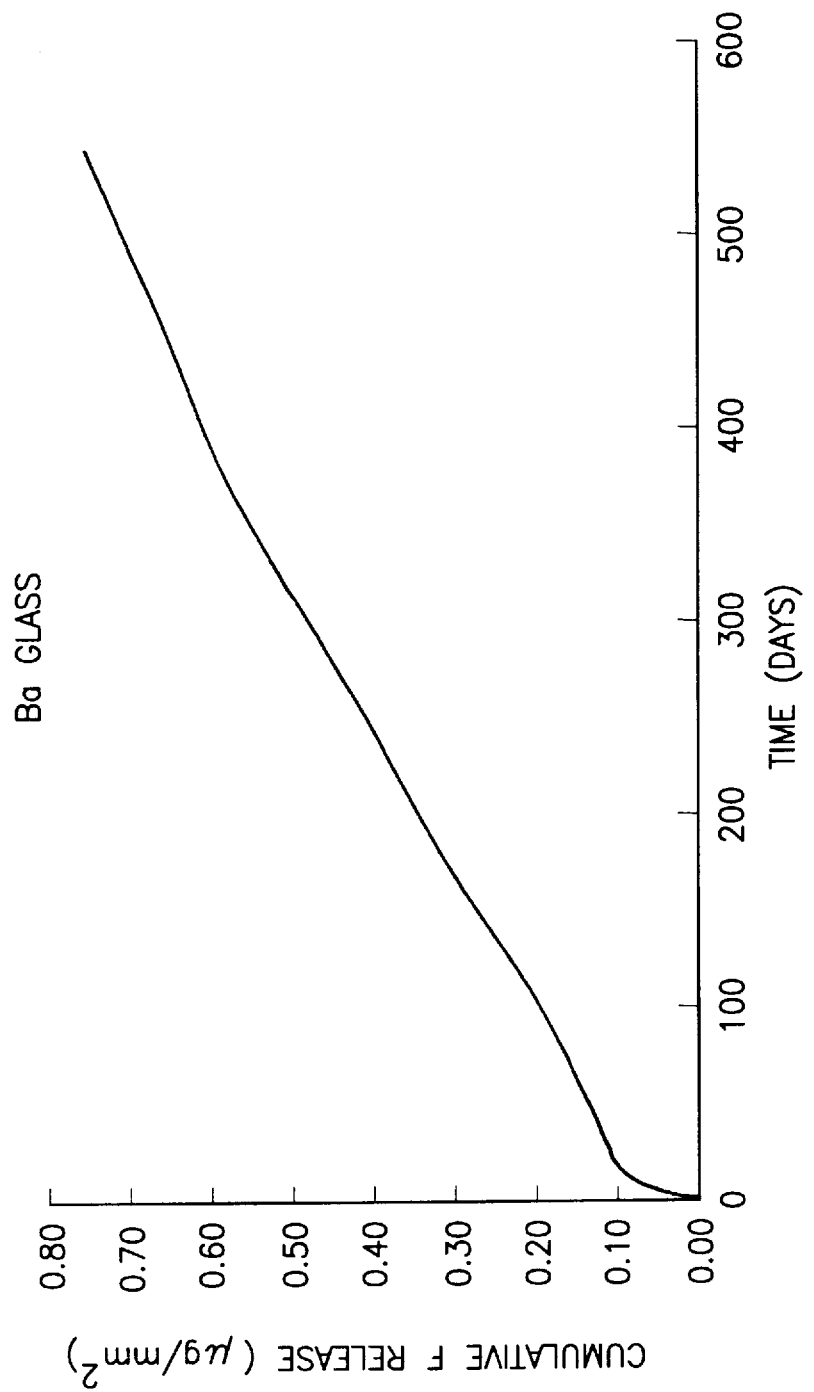
FIG. 1 is a graph showing the uniform, long term leaching of fluoride from a fluoride source used in making a primary coating.

The invention contemplates a broad-based treatment of the non-dental-related parts of the human and domestic animal anatomies. The treatment of the invention can be used in all manners to aid natural healing of all the various non-dental-related osseous materials and wounds, and achieve biocompatibility of non-dental-related foreign objects placed within and on the body, and the like. For example, the invention relates to an improvement in the treatment of solid surfaces exposed or involved in a non-dental-related surgical operation. In particular, the invention is primarily concerned with i.) the adhesion and biocompatibility of one osseous surface within a body (animal) to another and its biocompatibility with attached connective tissue and the surrounding tissue environment, such as in the setting of bone fractures that require incisions to the skin to get at the fracture, the repair of bone caries, the implantation of materials containing fluoride into bone to aid in the regrowth of bone tissue, and the like;

ii.) the adhesion of a prostheses surface made of metal, plastic and/or ceramic, to an osseous surface and/or its biocompatibility with attached connective tissue and the surrounding tissue environment, such as in hip joint replacements, knee joint replacements, pin and staple insertions in bone, bone implanted metals such as titanium, stainless steel, and the like, to reinforce the bone, and the like;

iii.) the adhesion and biocompatibility of a prostheses surface made of metal, plastic and/or ceramic, to tissues that it contacts, such as an artificial pacemaker, their leads and electrodes, subcutaneous implants, plastic hip joint replacements made of metal, ceramic and such plastics as poly(arylether)sulfone, polyarylsulfones, and other related engineering polymers, and the like;

iv.) aiding in the healing of non-dental-related soft tissue such as by placing a film of the primary coating with fluoride or a thermoplastic film containing a source of water leachable fluoride by placing such films in contact with the injury and allowing fluoride to leach from the film and contact the region of the injury.

The Primary Coating

The primary coating is typically a crosslinked heat and/or light set resin that contains hygroscopic groups that attract water to the coating. When the crosslinking is not too extensive, the primary coating can absorb enough water that it can swell. The amount of water that the primary coating can absorb can be as high as 37 weight percent. However, the degree of crosslinking of the primary coating is typically high enough that water absorption (determined according to ADA Specificaton No. 27) will not exceed about 10 weight percent, preferably not exceeding about 7 weight percent. The backbone of the polymer providing the hygroscopic groups of the resin phase of the primary coating is typically aliphatic and may contain groups therein that enhance the hydrophilicity of the resin phase. Though the primary coating's resin can be made by a condensation reaction, such as by low temperature resin formation by the reaction of a blocked polyisocyanate with a polyol, the resin is typically the in situ reaction product of one or more of a polymerizable ethylenically unsaturated organic monomer containing groups that are attractive to water. Thus the components of the primary coating may be (a) an ethylenically unsaturated-functional monomer that contains a hygroscopic group. Typical of such groups are hydroxyl, amide, amine, aliphatic ether, amine, hydroxyalkyl amine, hydroxyalkyl amide, pyrrolidone, ureyl, and the like. Illustrative of such monomers are the following:

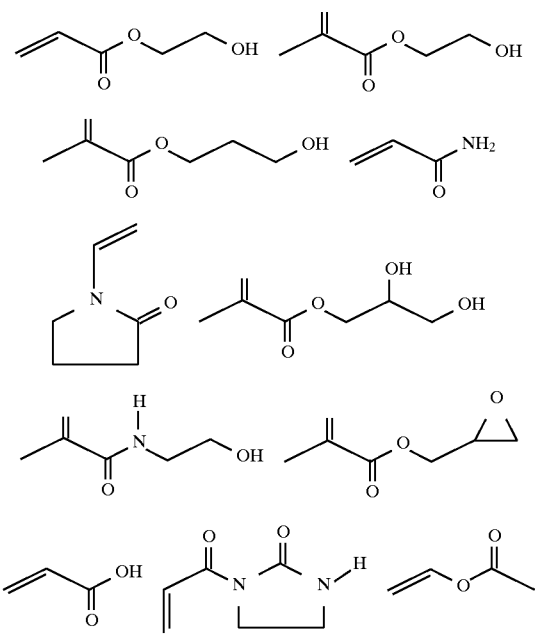

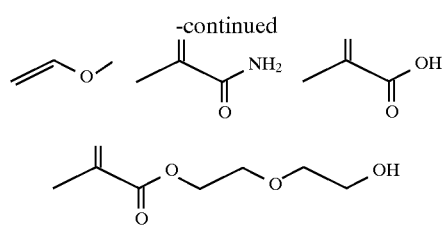

A particularly desirable ethylenically unsaturated-functional monomer is an acrylic-type monomer having the following structure:

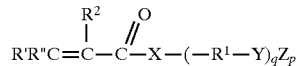

wherein R' and R", individually, are hydrogen, alkyl of 1 to about 4 carbon atoms, monocyclic aryl, such as phenyl, alkyl phenyl where the alkyl is 1 to about 3 carbon atoms, cyclohexyl, and the like; $R^2$ is hydrogen, alkyl of 1 to about 3 carbon atoms, and the like; X is O, S and N—$R^3$, where $R^3$ is hydrogen, alkyl of 1 to about 4 carbon atoms, —$R^1$—Y, and the like; $R^1$ is a divalent radical connecting Y to X, and may be one of the following:

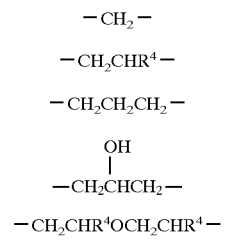

wherein each $R^4$ is hydrogen or alkyl of 1 to about 3 carbon atoms; and Y is OH, $NR^5$, SH, $OR^6$, where $R^5$ is hydrogen, methylol, methylol methyl ether, $R^6$ is alkyl of 1 to about 3 carbon atoms provided that $R^1$ is —$CH_2$—, and the like; q is 0 or 1 and p is 0 or 1, and p is 0 when q is 1 and 1 when q is 0; Z is hydrogen.

A particularly desirable thermosetting coating is based on 2-hydroxyethyl methylmethacrylate ("HEMA"), 2-hydroxyethyl acrylate, 2,3-dihydroxypropyl methacrylate, acrylamide, methacrylamide, hydroxyalkyl acrylamide, hydroxyalkyl methacrylamide, and the like materials.

(b) A linear polycarboxylic acid or acid salt that contains a plurality of pendant carboxyl or carboxylic acid salt groups such as one having the formula:

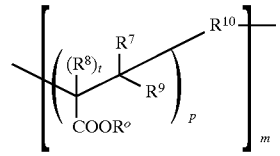

$R^o$ is hydrogen or alkali metal, such as Li, Na, K, Ru and Cs to form a salt, and preferably hydrogen, sodium or potassium, $R^7$ and $R^8$ are hydrogen or alkyl containing from 1 to about 3 carbon atoms, $R^9$ is hydrogen, alkyl of 1 to about 3 carbon atoms, or $COOR^o$, provided that $R^9$ is not alkyl when $R^7$ is alkyl, $R^{10}$ is a valence bond when the formula is for a homopolymer or a divalent organic moiety of a polymerized ethylenically unsaturated monomer, p is a number representing at least 40 mole percent of the units of the polymer, and m is a number providing for a molecular weight of from about 2,000 to about 500,000. Particularly preferred polycarboxylic acids are polyacrylic acid, polymaleic acid, polyitaconic acid, or a copolymer of acrylic acid, maleic acid, fumaric acid or itaconic acid with other ethylenically unsaturated monomers such as methyl acrylate, ethylacrylate, methylmethacrylate, vinyl acetate, vinylmethylether, styrene, α-methylstyrene, vinylcyclohexane, dimethylfumarate, ethylene, and the like. Preferably, these polymers have molecular weights $M_w$ of about 3000–250,000. In one embodiment, the polycarboxylic acid or the salt form may contain about 1–5 weight % of d-tartaric acids.]

(c) A desirable coupling agent is an acrylic-type monomer that possesses acrylic-type unsaturation and contains a surface bonding group possessing one or more of the following groups:

| | | | |
|---|---|---|---|
| i) | an alkylene polyether; | vi) | tertiary amine |
| ii) | hydroxyl | vii) | phosphoryl |
| iii) | carboxyl | viii) | phosphinyl |
| iv) | carboxylic acid salt | ix) | stannoyl |
| v) | quaternary ammonium | x) | amide |
| | | xi) | alkylene amine |

A preferred coupling agent is a simple aromatic substituted amino acid or its alkali metal salt such as the free acid or alkali metal salt of (i) N-phenylglycine, (ii) the adduct of N-(p-tolyl)glycine and glycidyl methacrylate, which are illustrated by the structures:

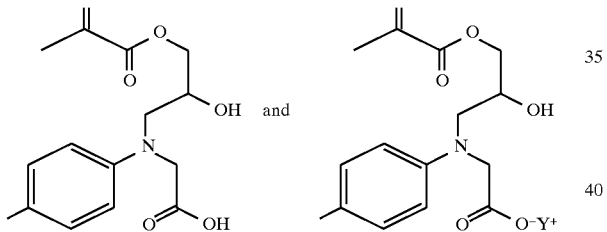

where Y is one of the alkali metals, i.e., lithium, sodium, potassium, rubidium and cesium, preferably sodium or potassium, and (iii) the adduct of N-phenylglycine and glycidyl methacrylate, the alkali metal salt thereof, or the mixture of the foregoing two compounds, which compounds are illustrated by the structures, and (iii) the adduct of N-phenylglycine and glycidyl methacrylate, which are illustrated by the structures:

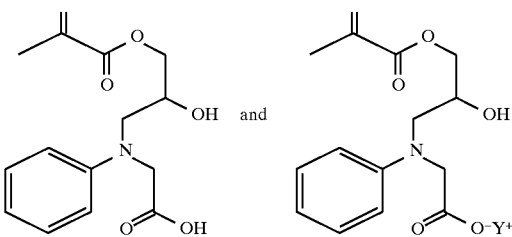

where Y is described above; or the mixture of the foregoing two compounds, alone or in combination with a compound containing at least one group or moiety capable of free radical polymerization and at least one aromatic ring or moiety containing one or more electron-withdrawing substituent that does not interfere with free radical polymerization.

The purpose of the coupling agent is to interreact with the polymerization of the aforementioned ethylenically unsaturated-functional monomer that contains a hygroscopic group and enhance wetting by the resulting resin of proteinaceous surfaces by the surfaces interaction with the carboxylic acid or carboxylic acid salt group in the bonding agent.

(d) A number of acrylic coating resins rely on polyacrylyl substituted monomers to crosslink and chain extend the polymer that comes into existence on polymerization in the presence of an polymerization initiator. For example, the pure forms of HEMA typically contain small amounts of ethylene glycol dimethacrylate which will crosslink a polymer based on HEMA. The degree of crosslink may be so minuscule as to have little effect on the ultimate properties of the polymer. Crosslinking agents are frequently added to HEMA based resins to impart a particular quality of crosslinking and toughness to the cured resin. For example, diethylene glycol dimethacrylate can otherwise lower the crosslink density of the resin which may impart toughness to the resulting cured polymer. Those types of crosslinkers would be considered a soft crosslinker, as defined above. However, in the practice of this invention, it is desired to use dual crosslinkers, one that is hard and one that is soft. In this respect, one may include the above crosslinker, in its normal impurity concentrations, as part of the soft crosslinker, but in the preferred embodiment, it is desirable to employ hard and soft crosslinkers that contain at least two acrylyl groups bonded to aromatic containing moiety(ies). A desirable hard crosslinker is characterized by the following formulae:

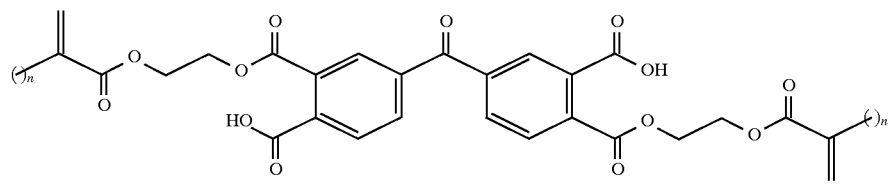

"A"

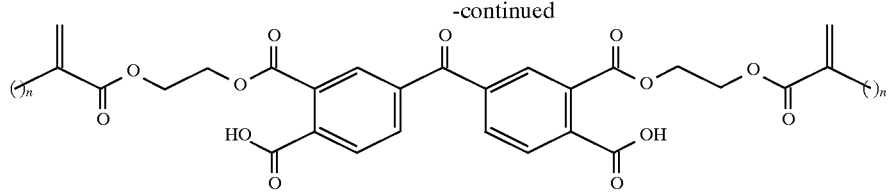
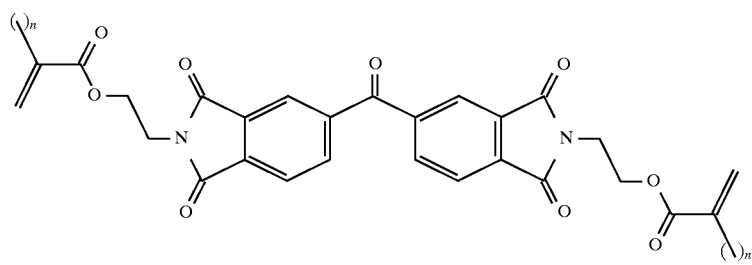
"B"
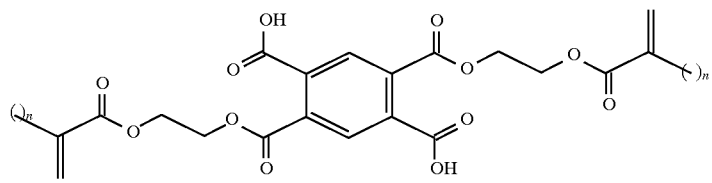
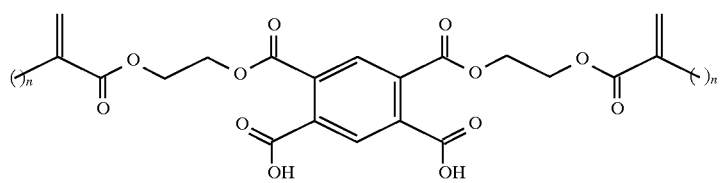
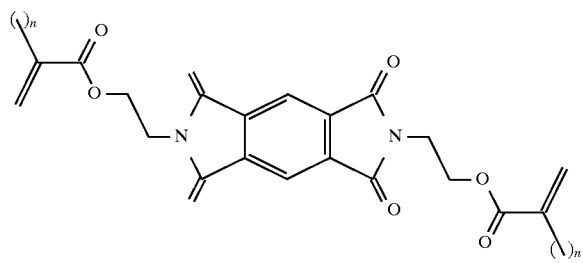
"C"
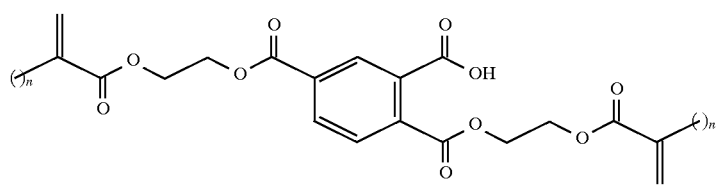
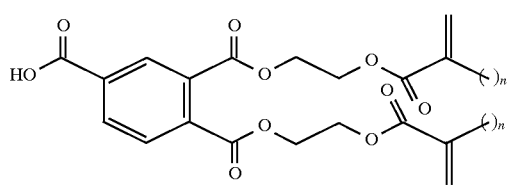
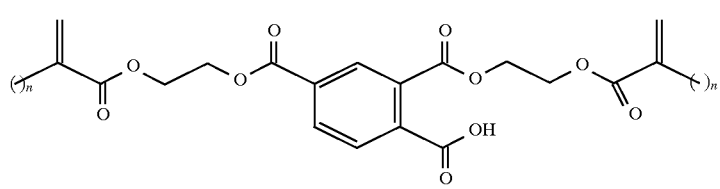

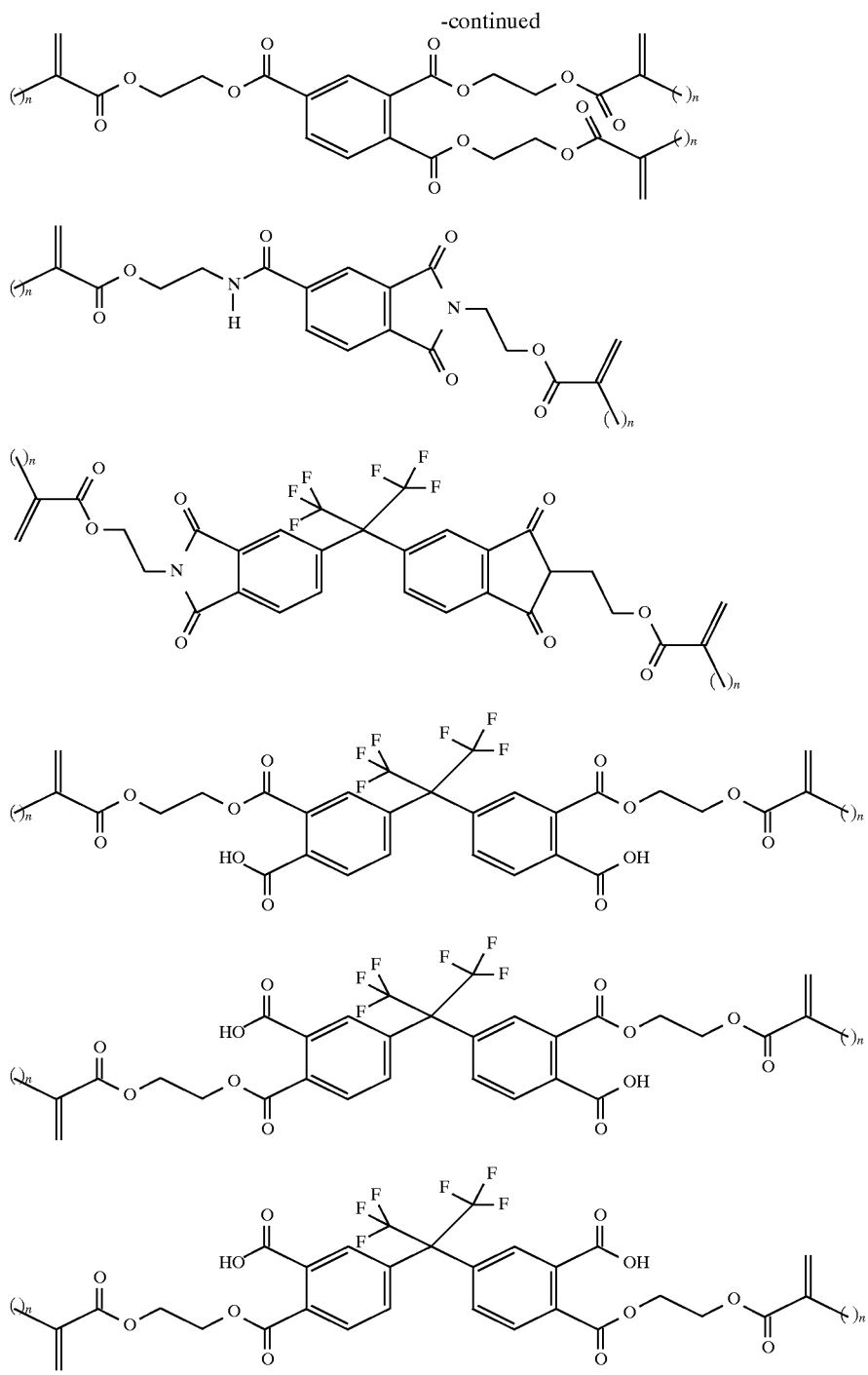

"D"

wherein n is 0 or 1. The preferred hard crosslinking agent is one of (i) the esters or imides of pyromellitic acid dianhydride and 2-hydroxyethyl methacrylate or 2-aminoethyl methacrylate, or the corresponding acrylates, as illustrated in group B above, (ii) the ester or imides of 3,3', 4,4'-benzophenonetetracarboxylic dianhydride and 2-hydroxyethylmethacrylate or 2-aminoethyl methacrylate, or the corresponding acrylates, as illustrated in group A above, (iii) the esters and imide/amides of 4-trimellitic acid anhydride and 2-hydroxyethylmethacrylate or 2-aminoethyl methacrylate, or the corresponding acrylates, as illustrated in group C above, (iv) the ester or imides of 2,2-bis(3,4,-dianhydridophenyl)-1,1,1,3,3,3-hexafluoropropane and 2-hydroxyethyl methacrylate or 2-aminoethyl methacrylate, or the corresponding acrylates, as illustrated in group D above, and (iv) other compounds containing at least one group or moiety capable of free radical polymerization and at least one aromatic ring or moiety containing electron-withdrawing substituents that do not interfere with free radical polymerization. The soft crosslinker is typically an diacrylic or dimethacrylic ester or ether of bisphenol A, but also include as soft crosslinkers are the other glycol dimethacrylates and diacrylates mentioned herein. Preferred soft crosslinkers are ethoxylated bisphenol A dimethacrylate and the adduct of glycidylmethacrylate and bisphenol A, (e) The fluoride component is present in the primary coating as a component of a non-resinous component of the formulation. The fluoride component may be, but need not be soluble in the resin component of the primary coating. In the preferred practice of the invention, the fluoride component in the primary coating will dissolve in water and to the extent the water is removed from the fluoride source, fluoride is carried with it. As noted above, the particularly desirable form of the fluoride component, is an inorganic fluoride in which the fluoride is present, e.g., in the form of an fluorosilicate structure or an alumina fluoride structure. The fluoride source of the patent is a glass composition in which the fluoride content is derived from an alkaline earth metal fluoride such as calcium fluoride, barium fluoride and strontium fluoride. A most preferred fluoride source is described in U.S. Pat. No. 5,360,770 which is incorporated herein by reference, particularly the examples and illustration of the patent that show how to make the fluoride source. As noted above, the primary coating is optionally provided with a leachable fluoride component. The fluoride is leachable from the coating over a three to four month period. This means that after many days and even months, the coating should be able to release small measured amounts of fluoride into the wound area. The longevity of the fluoride in the coating and the ability to meter it from the coating are dependent on a number of factors, such as:

the concentration of fluoride in the coating;

the nature of the chemical bond of the fluoride within the coating composition;

the level of hygroscopicity of the coating;

if the fluoride is part of a solid, the degree of particulateness of the solid, coupled with the rate at which fluoride can be leached from the solid;

if the fluoride is part of a liquid molecule, the rate at which the fluoride is cleaved from the molecule to form a leachable fluoride; and if the fluoride is part of a polymer, the rate at which fluoride in the polymer can be solubilized and leached from the polymer.

A particularly desirable form of the fluoride component, is an inorganic fluoride in which the fluoride is present, e.g., in the form of an fluorosilicate structure or an alumina fluoride structure. Illustrative of such fluoride structures are fluorite (or fluorspar), $CaF_2$, $BaF_2$, $SrF_2$, cryolite, $Na_3AlF_6$, and fluorapatite, $3Ca_3(PO_4)_2Ca(F,Cl)_2$. A preferred fluoride source is described in U.S. Pat. No. 5,360,770. The fluoride source of the patent is a glass composition in which the fluoride content is derived from an alkaline earth metal fluoride such as calcium fluoride, barium fluoride and strontium fluoride. A particularly preferred glass composition that provides fluoride is the following:

TABLE 1

| Component | Mole % | Component | Mole % |
|---|---|---|---|
| $SiO_2$ | 17.6–21.6 | $P_2O_5$ | 0.8–3.5 |
| $Al_2O_3$ | 9.0–11.0 | $Na_2O$ | 0.5–3.0 |
| MO | 7.9–19.7 | F | 42.2–56.1 | in which M is an alkaline earth metal and MO is barium oxide and barium oxide binary and ternary mixtures with other alkaline earth metal oxides, such as BaO, BaO—CaO, BaO—SrO and CaO—BaO—SrO. Such preferred source of fluoride not ocoating bues long term fluoride release from the primary coating but it also provides an essentially uniform release of fluoride over that period of time. FIGS. 1 and 2 illustrate the long term fluoride leachability of this fluoride source. FIG. 1 illustrates the release of fluoride by placing the aforementioned barium oxide based glass in water and determining the release of fluoride over an extended period of time. As can be seen, the fluoride release follows a straight line showing uniform release over 550 days, about 1½ years. FIG. 2 shows area plots of ingredients in order to optimize the glass formulation for maximizing the fluoride release over an extended period, e.g., 1½ years.

(f) Also included in the formulation, as an optional ingredient, is a photoinitiator. According to one aspect this invention, the light-initiated curing of a polymerizable matrix material involves photosensitization of light-sensitive compounds by ultraviolet or visible light, which, in turn, initiates polymerization of the matrix material. The photoinitiator to be used in this invention comprises a combination of a photosensitive ketone and a tertiary amine. Typical photosensitive ketones include benzophenone, acetophenone, thioxanthen-9-one, 9-fluorenone, anthraquinone, 4'-methoxyacetophenone, diethoxyacetophenone, biacetyl, 2,3-pentadione, benzyl, 4,4'-methoxybenzil, 4,4'-oxidibenzil, and 2,3-bornadione (dl camphroquinone). Typical tertiary amines include ethyl-4-dimethyl amino benzoate, ethyl-2-dimethyl amino benzoate, 4,4'-bis(dimethylamino) benzophenone, N-methyldiethanolamine, and dimethylaminobenzaldehyde. A preferred combination of the photoinitiators is 2,3-bornanedione with ethyl-4-dimethyl amino benzoate. Other suitable initiator are illustrated in U.S. Pat. No. 4,674,980 to Ibsen, et al., the disclosure of which is incorporated by reference. Alternatively, any known photosensitizing system which can function effectively in a paste/paste composition when exposed to light may substitute for the above-named compounds or combinations. The amount of the photoinitiator should be sufficient to initiate polymerization in a selected resin and complete it in depth within about half a minute when the filler-resin composition is exposed to a visible-light output of at least 5,000 foot candles. In addition, any known free-radical scavenger (anti-oxidants) such as butylated hydroxytoluene can be used to scavenge small amounts of free radicals generated during extended shelf storage.

(g) The polymerization system of the primary coating composition may depend on effecting cure with either the photoinitiator or by use of a thermal initiator, which is a typical thermal curing agent known in the art. Illustrative of these are benzoyl peroxide, dicumyl peroxide, ditertiary butyl peroxide, tertiary butyl hydroperoxide, cumyl hydroperoxide, or other suitable peroxides may initiate polymerization of the polymerizable ethylenically unsaturated components of the primary coating. Addition of such thermal initiators is desirable to insure complete polymerization. Even when light alone does not cure the matrix material, the peroxide initiates curing of the uncured material thermally upon standing. Benzoyl peroxide may be used together with 2-hydroxyethyl-p-toluidine.

The primary coating may contain pigments such as iron oxide or titanium oxide and a color stabilizing agent such as 2,2-hydroxy-5-tert. octyl phenylbenzotriazole.

In formulating the primary coating, the selection of the ingredients in formulating the coating is narrowly critical.

Illustrative of such a formulation is the paste/paste primary coating composition as set forth in Table 2.

TABLE 2

| Ingredients | Percentage by Weight |
|---|---|
| Paste A | |
| Glass, fluoride source | 0–85 |
| Ethylenically unsaturated monomer, e.g., 2-hydroxyethyl methacrylate | 3–40 |
| Soft Crosslinker, e.g., Ethoxylated bisphenol A dimethacrylate | 10–60 |
| 2,3-bornanedione | 0.03–0.30 |
| Butylated hydroxytoluene | 0.001–1.0 |
| Benzoyl peroxide | 0.005–0.10 |
| Polycarboxylic acid, e.g., polyacrylic acid | 0–8 |
| Hard Crosslinker, e.g., PMDM | 2–20 |
| d-Tartaric acid | 0–1 |
| 2,2-Hydroxy-5-tert-octyl phenylbenzotriazole | 0.00–2 |
| Ethyl 4-dimethylaminobenzoate | 0.00–2 |
| Paste B | |
| Glass, fluoride source | 0–70 |
| Ethylenically unsaturated monomer, e.g., 2-hydroxyethyl methacrylate | 0–45 |
| Soft Crosslinker, e.g., ethoxylated bisphenol A dimethacrylate | 10–90 |
| Coupling agent, e.g., Na NTG-GMA, NGT-GMA | 1–20 |
| Zinc oxide | 0–15 |
| Barium tungstate | 0–15 |
| Ethyl 4-dimethylamino benzoate | 0–2.0 |
| 2,3-bornanedione | 0.05–0.30 |
| Butylated hydroxytoluene | 0.005–0.10 |
| Titanium dioxide | 0.0–3.0 |
| 2,2-Hydroxy-5-tert-octyl phenylbenztriazole | 0.00–2 |

The two pastes, Paste A and Paste B, are preferably mixed well in equal amounts. The pastes may be mixed with a spatula or put onto a blade mixer prior to application to a surface. For example, the physician or technician may use the system by combining the pastes in the ratios desired, and then mixing them. The resulting paste is then applied to the surface as needed. The coating will self-cure in about 20–30 minutes, but cures instantly on exposure to light. Light having a wave length of about 480 ηM at an intensity of about 5000 foot-candles is preferred. An exposure of about 30 second is sufficient to cure the cement in most applications.

As noted above, a primer coating may be applied to the treated surface before coating on the primary coating. This may be effected by the following procedure:

(1) First contacting the surface with an aqueous solution comprising at least one strong acid or acidic salt with a dispensable brush or a skube (a preformed Styrofoam™ sponge) in order to condition the surface, Leave for 15 seconds and blot dry with a skube. Note: if hemorrhage is in the area, use a hemostatic solution or the aqueous solution with a hemostatic solution to control seepage and keep the bonding surface dry.

(2) Immediately mix with stirring with a dispensable brush a solution comprising a solvent and at least one compound selected from the group consisting of (1) N-phenylglycine, (2) the adduct of N-(p-tolyl)glycine and glycidyl methacrylate, (3) the addition reaction product of N-phenylglycine and glycidyl methacrylate, and (4) other amino acids, in which each member of the group of (1), (2), (3) and (4) that is present in the solution is an alkali metal salt form of that member, and a solution comprising at least one monomer selected from the group consisting of (1) the addition reaction product of pyromellitic acid dianhydride and 2-hydroxyethyl methacrylate, (2) the addition reaction product of 3,3', 4,4'-benzophenone tetracarboxylic dianhydride and 2-hydroxyethyl methacrylate, (3) 4-methacryloxyethyltrimellitic-anhydride, and (4) other compounds containing at least one group or moiety capable of free radical polymerization and at least one aromatic ring or moiety containing electron-withdrawing substituents that do not interfere with free radical polymerization. Apply 3–5 coats of the mixture onto the prepared bonding surface with the dispensable brush used for mixing. Allow to dry for 15 seconds.

(3) Mix Paste A and B together and load into a syringe. Immediately inject the paste mixture onto the prepared bonding surface and light-activate for 30 seconds. This will effect cure.

The above procedure can be effected without using the primer coating. In such an embodiment, it is important to clean the surface to which the primary coating is being applied. Water washing the surface if an acid wash is not recommended or needed will prepare the surface provided the surface is thoroughly dry before applying the primary coating.

As noted above, the invention can involve forming a cured patch of the primary coating on glass or Teflon® with a knife coater. The coating should be as thin as workable, such as from about 1 to about 100 mils. The patch may have a thickness of about 0.75 mil to about 95 mils, preferably from about 2 to about 50 mils. Its length and width is dependent upon where the patch is to be employed. For example, the patch can be inserted into the linea aspera femoris (within the femur) at the site of a fracture or at the site of a prosthesis inserted into the femur. Because the patch is biocompatible, it is not rejected and, as such, will aid the natural growth of new bone without infection. This is particularly the case where the patch contains fluoride.

In another embodiment, a Gortex® permeable membrane similar porous membranes or films coated with the primary coating can be used as a bandage for the treatment of wounds. The uncured primary coating is applied to a side of the membrane and the membrane is applied to the wound. Heating of the membrane causes the primary coating thereon to cure in situ.

The primer coating may contain solvent solutions of the free acid or alkali metal salt of (i) N-phenylglycine, (ii) the adduct of N-(p-tolyl)glycine and glycidyl methacrylate, which are illustrated by the structures:

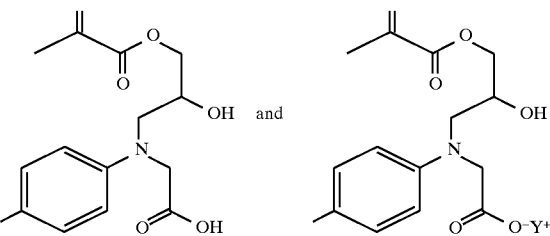

where Y is one of the alkali metals, i.e., lithium, sodium, potassium, rubidium and cesium, preferably sodium or potassium, and (iii) the adduct of N-phenylglycine and glycidyl methacrylate, the alkali metal salt thereof, or the mixture of the foregoing two compounds, which compounds are illustrated by the structures, and (iii) the adduct of N-phenylglycine and glycidyl methacrylate, which are illustrated by the structures:

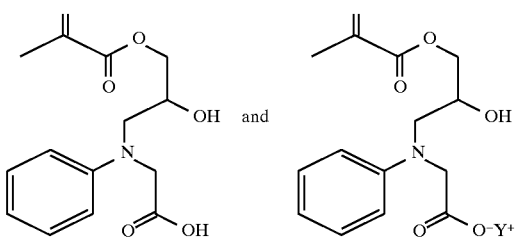

where Y is described above; and the solvent solution of PMDM (see the isomeric mixture of "B" above that describes the adduct of pyromellitic acid dianhydride and 2-hydroxyethyl methacrylate). The preferred solvent is a mixture of water and a polar solvent such as acetone.

When applying the primer coating, the surface may be prepared with an acid wash as disclosed in the aforementioned reissue application. The first stage of the primer coating may be a solvent solution of the NTG-GMA adduct, typically dried before the second solution is applied to it. The second stage is a solution of, e.g., PMDM that is coated over the first stage. That coating is also dried before applying the primary coating. On drying, the primer coating is cured. Drying may be effected at ambient conditions, or accelerated by the addition of heat to the undried coating.

The process of this invention is effected by applying the primary coating with or without the primer coating, on an non-dental-related anatomical surface of a human or domesticated animal that is undergoing normal healing or surgical repair or to a prosthesis that is placed within the non-dental-related anatomy of a human or domesticated animal. For example, the process of the invention can be used in bone fractures where an incision is needed to effect surgical repair to the fractured bone or the fracture is compounded thereby exposing the fracture bone through the skin. In those cases, the primary coating may be brushed or injected with a conventional hypodermic needle from a conventional hypodermic syringe onto and within the fracture. The fracture can then be set aided by the adhesive nature of the primary coating. Bone growth then occurs through and about the sites of the fracture to which the primary coating is applied without rejection of the coating. The result of the procedure is that the patient is more quickly able to operate the fractured body part thereby accelerating the patient's recovery. FIG. 3 shows a variety of fractures to which the primary coating may be applied. In the case of fractures, and other injuries below skin surface, the primary coating may be subcutaneously injected by a syringe and needle to a fracture that has not broken skin or does not require an incision. In that embodiment, the fracture, located by x-ray, can be treated by having the injection place the coating at the fracture point. The injected primary coating is allowed to penetrate the fracture point. Cure of the primary coating is allowed to take place by placing a heating pad over the fracture and heating the site to a temperature of about 50° C. for a short time to kick off the curing agent in the coating. One the curing process is initiated, which is an exothermic reaction, it is just a question of a few days to effect full cure. In another embodiment, the primary coating can be heated while in the syringe to a curing temperature, and before setting can take place, the primary coating, as a paste or liquid, can be injected subcutaneously or to an open fracture, to be set at the site of the fracture. Before any primary coating is allowed to be cured (i.e., brought to a thermoset condition), the fracture must be set so that on cure, the primary coating holds the bone in the desired position for proper bone healing and configuration. FIG. 3A illustrates a comminuted bone fracture 1 in which comminuted bone fracture 10 of bone 8 can be set in the normal manner, and to which can be applied, subcutaneously via a syringe and needle 12, the primary coating. In this approach, the primary coating is allowed to penetrate to fracture site 10 and be absorbed into the bone at fracture site 10. Curing of the coating can be effected by applying heat to the outside of the bone as pointed out above, and/or by applying the primary coating in a heated condition at the time of injection, also pointed out above. Heat application is minimized in order to avoid inflammation of the tissue at the site of the wound. On the primary coating is applied and cure is initiated, it is desirable to apply ice packs to the site of treatment in order to calm the inflammation. FIG. 3b illustrates a compound fracture 2 where the bone 16 penetrates the skin 14 of the patient. Again, the primary coating may be injected via syringe and needle 18 into the bone interior at the site of the fracture. Then the bone is set in the normal fashion, heat is applied, as stated above to cure the primary coating. The primary coating may be applied to any skin wound that is associated with the fracture in order to facilitate the healing of the wound. In FIG. 3C, involving a spiral bone fracture 3 to bone 20, a patch 24, formed by coating a thin film of the primary coating on glass or another release surface such as Teflon® and cutting to the desired size and shape, e.g., a rectangle of 5 mils thickness and a width of 0.25 and a length of 0.5 cm, may be applied within the fracture or wound at 22, or adjacent the fracture or wound especially if the primary coating contains leachable fluoride. The thin film can be held in position within the bone by applying a paste 26 of the primary coating onto the bone or patch and using the primary coating paste to adhere the patch to the facture. Heating and cooling is applied as recommended above to cure the coating and to relieve inflammation.

FIG. 4 illustrates an implanted prosthesis 4. For example, FIG. 4 illustrates a hip socket prosthesis 30. The hip is a ball-and-socket joint; the ball is the spherical head of the thighbone, or femur 34, and the socket is a region on the side of the hipbone known as the acetabulum 28. The prosthesis 30 replaces the ball of the conventional spherical head of the femur and is bonded via rod section 32, inserted into femur 34.

Friction between the bones of the hip joint is reduced by a coating of cartilage and by a lubricating agent known as synovial fluid. Thus, effective biocompatibility between the prosthetic ball of the device is important to the function of the device. Injuries to the hip joint are common. In athletic injuries involving severe trauma, the head of the femur may be torn out of its normal position in the acetabulum by the force of the injury, causing dislocation. In older people, injuries, even relatively minor ones, may cause a fracture of the neck of the femur, the small portion that lies just below the head. In addition, the hip joint is subject to tuberculosis and to a variety of inflammations and degenerative changes in arthritis. Hip joints severely damaged by falls or arthritis are now often removed and replaced with an artificial hip joint that allows nearly normal activity in most persons.

This prosthetic device may be made of metal, ceramic or plastic. Preferably, the device is made of a strong metal such as titanium and titanium alloys, or of steel and steel alloys. The coating may be brushed on and then heated to give a smooth thin coating that enhances biocompatibility of the metal surface to the surrounding tissue. In particular, the other end of the device, representing the neck of femur may be inserted into the upper part of the femur by wedging an extension of the artificial neck of femur, such as rod, into the interior of the femur, or a clamp that is clamped about the exterior of the femur. The rod or clamp can be coated with the primary coating before wedging the rod in the femur or placing the clamp about the femur so as to create an uncured primary coating interface between the metal surface of the device and the femur. Alternatively, the device may be installed without a coating and the coating is applied in situ by brush or by injection using a syringe and needle. Then the coating can be heated and cured. The primary coating thus acts as a tough and strong adhesive for the device while also enhancing biocompatibility. The primary coating does not inhibit bone growth and normal healing over the device inserted into or clamped to the femur.

FIG. 5 illustrates a schematic view of a battery driven heart pacemaker in which the device 36 and all of the leads 38, 40 are coated with a primary coating in order to enhance the biocompatibility of the surfaces within the body.

FIG. 6 shows a catheter prosthesis 6 to which the primary coating can be applied in order to enhance biocompatibility of catheter 6 in the body. In carrying out an angioplasty operation in which a balloon catheter is inflated inside an artery, stretching the intima and leaving a ragged interior surface after deflation, which triggers a healing response and breaking up of plaque, the invention involves two features:

1. The coating is applied to the balloon 50 and the catheter surfaces 42 and cured, to aid in the biocompatibility of the catheter and balloon to the environs of the vessel,
2. The coating 54 is applied to unexpanded balloon 50 and left uncured, then catheter 6 is positioned by conventional procedures, in the intima where blockage of the surface is being treated. Balloon 50 is expanded to balloon position 52 with a heated gas fed through lumen 44 to interior 48 of balloon 50, causing contact with the plaque blockage. While in contact with the blockage, the uncured coating impregnates the plaque. Heating cures the primary coating in situ and this causes the plaque to become encrusted by the cured coating. This prevents the broken plaque from being captured in the blood stream and being the basis for heart blockage and subsequent stenosis or occlusion of a feeding vessel. In a preferred embodiment, the catheter of choice may be a double balloon catheter in which each balloon is located on the same tube, one upstream of the other, each separately gas fed through independent feed lumens within the tube. The lumen feeding the forward balloon is inflated by a body temperature fluid, and the lumen feeding the rearward balloon is inflated by a heated fluid. The rearward balloon is coated with a thick pasty uncured coating of the primary coating, and the catheter is inserted at the intima undergoing angioplasty. The forward balloon is positioned between the blockage being treated and the heart and the second balloon with the pasty coating is placed at the site of the blockage. Both balloons are expanded or the rearward balloon is expanded until the pasty primary coating is in contact with the plaque and the plaque is compressed, coupled with heating of the balloon to the curing temperature of the primary coating. After setting takes place, the rearward balloon is deflated and the forward balloon is inflated if it was not already inflated. The catheter is withdrawn with the forward balloon inflated to rub across the coated area of the intima and clean the coating and the encrusted plaque from the intima. The forward balloon can be slowly deflated while the debris from the treatment is carried out of the vessel and into a main artery or totally removed from the body. In a preferred alternative of this embodiment, instead of a forward balloon, there may be employed an umbrella filter screen 56 made of a fine mesh material with a soft material 58 at its outer periphery, such a fine mesh polypropylene plastic filter shaped in the form of an expandable umbrella 56 with a soft foam material 58 glued to the edges and the struts of the umbrella. The umbrella screen 56 can be opened at the time of compaction to position 60 by feeding biocompatible gas through lumen 46 to assert pressure on the struts of umbrella 56, forcing open unbrella 56. The rearward positioned balloon 50, already coated with the primary coating paste 54 is expanded by heated gas fed through lumen 44 into balloon interior 48 to reach position 52. After compressig the plaque and impregnating the plaque with paste 54, the coating is cured as described above. Umbrella 56 is opened (or already in the open position) while catheter 6 is removed from the site of compaction. The opened mesh-like filter umbrella 56 removes the treated plaque which is agglomerated by virtue of curing paste and is easily recovered in the filter.

The primary coating, alone or in combination with the primer coating, can be applied to a variety of prosthetic devices that serve as an artificial substitute for a missing body part, such as an arm or leg, used for functional or cosmetic reasons, or both. For example, the primary coating can be applied to working and non-working surfaces of the device that come into contact with live tissue. Illustrative of such devices are antireflux prosthesis—a ring-shaped device that is placed around the esophagus above the stomach and below the diaphragm for treatment of gastroesophageal reflux and hiatal hernia.

Austin Moore prosthesis—a metallic implant used in hip arthroplasty.

Charnley's prosthesis—an implant for hip arthroplasty consisting of an acetabular cup and a relatively small femoral head component that form a low-friction joint.

cleft palate prosthesis—a prosthetic device, such as an obturator, used to correct cleft palate.

heart valve prosthesis—an artificial substitute for a cardiac valve; for various types, see below.

maxillofacial prosthesis—a prosthetic replacement for those regions in the maxilla, mandible, and face that are missing or defective because of surgical intervention, trauma, pathology, or development malformations.

penile prosthesis—a semirigid rod or inflatable device implanted in the penis to provide an erection in men with organic impotence.

Thompson prosthesis—a Vitallium® implant used in hip arthroplasty.

As noted above, the primary coating of the invention can be used with a variety of prosthetic valves used in the body. For example, the primary coating with or without fluoride may be applied to a variety of artificial cardiac valves to enhance their biocompatibility and as an adhesive for bonding to tissue. The primary coating may be applied to a Carpentier-Edwards™ valve, which is a porcine valve mounted on an Elgiloy alloy stent with a Teflon® cloth-covered sewing ring;

Hancock™ valve, which is a porcine valve mounted on a semiflexible stent made of a Stellite® ring and flexible struts of polypropylene;

Ionescu-Shiley™ valve, which is a cardiac valve substitute comprising glutaraldehyde-fixed bovine pericardium constructed as a three-cusp valve mounted on a Dacron®-covered titanium frame;

Lillehei-Kaster™ valve which is a tilting-disk valve comprivalve housing, Teflovalve housing, Teflon® sewing ring, and flat, fre pyrolytic carbon disk that opens to 80 degrees.

Medtronic-Hall™ valve, which is a tilting-disk valve comprising a titanium valve housing an S-shaped disk guide strut, a Teflon® cloth sewing ring, and a centrally perforated pyrolytic carbon-coated graphite disk that opens to an angle of 75 degrees.

Omnicarbon™ valve which is a tilting-disk valve similar to the Omniscience valve but entirely coated with pyrolytic carbon, including the sewing ring.

Omniscience™ valve which is a modification of the Lillehei-Kaster tiltingdisk valve, having a curvilinear pyrolytic carbon disk suspended in a one piece titanium frame with fin-like projections and a Teflon® sewing ring.

St. Jude Medical valve which is a bileaflet valve with a Dacron® sewing ring and pyrolytic carbon leaflets and housing, the leaflets opening to 85 degrees.

Smeloff-Cutter™ valve which is a caged-ball valve with two open titanium cages, one on each side of the valve ring, a barium-impregnated silicone rubber ball, and a Teflon® sewing ring.

Starr-Edwards™ valve which is a caged-ball heart valve prosthesis consisting of a Stellite® retaining cage containing a Silastic® ball and a Teflon® and polypropylene cloth-covered sewing ring.

Though this invention has been described with respect to a plurality of details, it is not intended that the invention be limited thereby except to the extent that such limitations appear in the claims. Other embodiments that are obvious variations of the embodiments herein disclosed are intended to be encompassed by this invention.

We claim:

1. A process for a non-dental-related wound treatment that comprises the step of applying, over a wound, a film or layer of a primary coating that comprises a hydrophilic water insoluble crosslinked resin coating, and, optionally, fluoride.

2. The process of claim 1 wherein the primary coating is cured as a thin film on a non-adhesive surface and is put in contact with the wound as a released film.

3. The process of claim 2, wherein the primary coating is coated on an adhesive receptive surface and cured, and then applied to the wound in the manner of a wound dressing.

4. A wound dressing comprising a primary coating that comprises a hydrophilic water insoluble crosslinked resin and, optionally, fluoride, that has been coated on an adhesive receptive surface and cured prior to application.

5. The wound dressing of claim 4 wherein the adhesive receptive surface is chosen from the group consisting of plastic and cloth.

6. The wound dressing of claim 5 wherein the adhesive receptive surface is a thermoplastic.

7. The wound dressing of claim 4 wherein the primary coating comprises fluoride.

8. The wound dressing of claim 4 wherein the adhesive receptive surface comprises a pressure sensitive adhesive.

9. A process for the treatment of a wound which comprises applying a wound dressing comprising a primary coating that comprises a hydrophilic water insoluble crosslinked resin and leachable fluoride dispersed therein onto an injured portion of a mammalian body, and allowing the fluoride to be released from the primary coating to contact and penetrate the injured area.

10. The process of claim 9, wherein the mammalian body is a human or a domesticated animal.

11. The process of claim 9, wherein the primary coating is formed from a thermoplastic hydrophilic resin that is water insoluble and the wherein the fluoride source is an inorganic fluoride from which the fluoride is leachable with water.

12. The process of claim 11, wherein the thermoplastic resin is a linear polymer that contains a hydroscopic group chosen from the group consisting of hydroxyl, carboxylic acid, amide, amine, aliphatic ether, hydroxyalkyl amine, hydroxyalkyl amide, pyrrolidone, and ureyl.

13. The process of claim 12 wherein the linear polymer comprises polymerized vinyl alcohol, polymerized hydroxyethylmethacrylate, or 2,3-dihydroxypropylacrylate.

14. The process of claim 13 wherein the linear polymer is chosen from the group consisting of a copolymers of vinyl alcohol and vinyl acetate, copolymers of vinyl alcohol and ethylene, copolymers of vinyl alcohol and acrylic acid, and polyacrylic acid.

15. In a non-dental-related surgical process wherein a repair is made by adhering one or more bones and/or prosthetic devices to each other and to any contacting soft tissue, the improvement being that the adherence of said bone(s) and/or prosthetic device(s) is accomplished by applying a primary coating comprising a hydrophilic water insoluble crosslinked resin containing both hard and soft crosslinkers and, optionally, fluoride, to one or more of the surfaces of the bone(s) or prosthetic device(s).

16. The process of claim 15 wherein a primer coating is provided on the surfaces before applying the primary coating.

17. The process of claim 15 wherein the primary coating contains fluoride that is released in small and safe quantities to the environ of the coating and the surfaces during the healing process.

18. In a non-dental-related surgical bone repair process comprising (i) incising skin to expose an area in which bone undergoing restoration resides, (ii) exposing the bone undergoing repair, (iii) defining within the exposed area the manner of restoration of the bone, (iv) preparing the area for said restoration, (v) effecting restoration, and (vi) closing the area after completion of the surgical procedure by closing the skin over the area and providing for the natural or aided healing of any wound associated with such procedure, the improvement being that, during said restoration, the following steps are followed in sequence:

(v)(a) selecting at least one bone surface within the exposed area that is to be bonded, (v)(b) coating that surface with a primary coating comprising a hydrophilic water insoluble crosslinked resin containing both hard and soft crosslinkers and, optionally, fluoride, (v)(c) contacting the coated surface with bone or a prosthetic device, (v)(d) curing the coating by exposing the coating to light or to ambient temperature.

19. In a non-dental-related surgical procedure to implant a prosthetic device within a body comprising (i) incising skin to expose an area of the body in which the prosthetic device is to be inserted, (ii) defining within the exposed area the manner of restoration therein by implantation of the prosthetic device, (iii) preparing the area for restoration,
(iv) effecting restoration,
(v) and closing the area after completion of the surgical procedure by closing the skin over the area and providing for the natural or aided healing of any wound associated with such procedure, the improvement which comprises, during said restoration, the following steps:
(iv)(a) selecting at least one prosthetic device surface within the exposed area that is to be bonded,
(iv)(b) coating that surface with a primary coating comprising a hydrophilic water insoluble crosslinked resin containing both hard and soft crosslinkers and, optionally, fluoride,
(iv)(c) contacting the coated surface with bone and/or tissue,
(iv)(d) optionally adding a patch of a cured film of the primary coating with fluoride, and
(iv)(e) curing the coating by exposing the coating to light or to ambient temperature.

20. In a non-dental-related process for aiding in the healing of an open wound or an exposed wound, the improvement which comprises superimposing a cured layer of a primary coating comprising a hydrophilic water insoluble crosslinked resin and fluoride onto the wound such that the tissues at the wound surface are in direct contact with the layer, and maintaining contact between the layer and the wound at least until such time as the wound is essentially closed as a result of the healing process.

21. In the process of claim 20 wherein the cured layer of primary coating with fluoride has, on one surface thereof, a layer of uncured primary coating with fluoride, and wherein the uncured primary coating is cured while both it and the cured primary coating are in contact with the wound by exposing the uncured primary coating to light and/or ambient temperature.

22. A non-dental-related process for repairing an injured or degenerated osseous material which comprises superimposing a patch of a cured layer of a primer coating comprising a hydrophilic water insoluble crosslinked resin with fluoride onto the injured or degenerated area of the osseous material, leaving such patch in contact with the area and allowing growth of the osseous material to encompass the patch and repair the injured or degenerated area.

23. In the process of claim 22 wherein the cured layer of primary coating with fluoride is formed having, one surface thereof, an uncured primary coating with fluoride, and wherein the uncured primary coating is cured while it and the associated cured primary coating are in contact with the area undergoing treatment by exposing the uncured primary coating to light and/or ambient temperature.

24. A process for enhancing the normal healing processes of injured non-dental-related soft tissue and non-dental-related osseous material, that involves placing at the injury a primary coating that is a hydrophilic water insoluble crosslinked resin coating that optionally contains a measurable amount of a water/fluid leachable fluoride capable of (a) being leached from the coating in a metered amount, and (b) transporting a small amount of leached fluoride from the coating into the afflicted area.

25. The process of claim 24 wherein the amount of fluoride provided in the primary coating is insufficient to cause fluorosis of any other toxic reaction, and the fluoride assists the normal processes of wound healing.

26. The process of claim 24 wherein the primary coating is one layer in a multilayer composite and wherein said composite further comprises a strongly adhesively bonded crosslinkable acrylic resin that rapidly that possesses less hydrophilicity than the primary coating and that cures in situ on an application surface to function as a primer for the primary coating.

27. The process of claim 24 wherein the resin is based on an ethylenically unsaturated functional monomer that contains a hygroscopic group.

28. The process of claim 27 wherein the ethylenically unsaturated functional monomer contains hygroscopic groups and exhibits hydrophilicity.

29. The process of claim 27 wherein the primary coating contains a polycarboxylic acid.

30. The process of claim 27 wherein the primary coating contains at least one crosslinking agent.

31. The process of claim 30 wherein the crosslinking agent is a combination of a hard crosslinker and a soft crosslinker.

32. The process of claim 27 wherein the primary coating contains a coupling agent.

33. The process of claim 27 wherein the primary coating contains leachable fluoride.

34. The process of claim 24 wherein the primary coating comprises a two component system that comprises:
(a) a first component comprising:
(1) a fluoride source including as a particulate siliceous fluoride containing filler in which the fluoride is water leachable;
(2) a coupling agent;
(3) a photoinitiator or a radiopaquing agent or a buffering agent; and
(b) a second component comprising:
(1) an ethylenically-unsaturated-functional monomer;
(2) a soft crosslinker;
(3) a hard crosslinker;
(4) a photoinitiator;
(5) a polymerized carboxylic acid;
(6) a free-radical scavenger; and
(7) a curing catalyst.

35. The process of claim 34 wherein the coupling agent is one or more of (i) N-phenylglycine, the alkali metal salt thereof, or the mixture of the foregoing two compounds, (ii) the adduct of N-(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds.

36. The process of claim 34 wherein the soft crosslinker is one or more of 2,2-bis(4-methacryloxy-2-ethoxyphenyl) propane, and diethyleneglycol-bis-methacrylate.

37. The process of claim 34 wherein the hard crosslinker is one or more of (i) the adduct of pyromellitic acid dianhydride and 2-hydroxyethylmethacrylate, (ii) the adduct of 3,3',4,4'-benzophenonetetracarboxylic dianhydride and 2-hydroxyethylmethacrylate, (iii) 4-methacryloxytrimellitic anhydride, and (iv) other compounds containing at least one group or moiety capable of free radical polymerization and at least one aromatic ring or moiety containing electron-withdrawing substituents that do not interfere with free radical polymerization.

38. A process for enhancing the biocompatibility and adhesion of bone and/or prosthetic devices involved in a non-dental procedure to tissue components with which they are in contact and wherein there is an injury, that involves placing at the injury or on the prosthesis a primary coating that is a hydrophilic water insoluble crosslinked resin coating containing both hard and soft crosslinkers and, optionally, a measurable amount of a water/fluid leachable fluoride capable of (a) being leached from the coating in a metered amount, and (b) transporting a small amount of leached fluoride from the coating into the afflicted area.

39. The process of claim 38 wherein the prosthesis is made of one or more of metal, ceramic or plastic.

40. The process of claim 38 wherein the amount of fluoride provided in the primary coating is insufficient to cause fluorosis of any other toxic reaction, and the fluoride assists the normal processes of wound healing.

41. The process of claim 38 wherein bone and/or prosthetic device surfaces in a non-dental-related surgical procedure, are joined by applying the primary coating or the primary coating with fluoride to bond one or more of the surfaces prior to completion of a surgical repair.

42. The process of claim 38 wherein the primary coating is one layer in a multilayer composite and wherein said composite further comprises a strongly adhesively bonded crosslinkable acrylic resin that rapidly that possesses less hydrophilicity than the primary coating and that cures in situ on an application surface to function as a primer for the primary coating.

43. The process of claim 38 wherein the primary coating comprises a resin based on an ethylenically unsaturated functional monomer that contains a hygroscopic group.

44. The process of claim 43 wherein the ethylenically unsaturated functional monomer contains hygroscopic groups and exhibits hydrophilicity.

45. The process of claim 43 wherein the primary coating contains a polycarboxylic acid.

46. The process of claim 43 wherein the primary coating contains a coupling agent.

47. The process of claim 43 wherein the primary coating contains leachable fluoride.

48. The process of claim 43 wherein the primary coating comprise a two component system comprising:

(a) a first component comprising:

(1) a fluoride source including as a particulate siliceous fluoride containing filler in which the fluoride is water leachable;
  (2) a coupling agent;
  (3) a photoinitiator or a radiopaquing agent or a buffering agent; and (b) a second component comprising:

(1) an ethylenically-unsaturated-functional monomer;
  (2) a soft crosslinker;
  (3) a hard crosslinker;
  (4) a photoinitiator;
  (5) a polymerized carboxylic acid;
  (6) a free-radical scavenger; and
  (7) a curing catalyst.

49. The process of claim 48 wherein the coupling agent is one or more of (i) N-phenylglycine, the alkali metal salt thereof, or the mixture of the foregoing two compounds, (ii) the adduct of N-(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds.

50. The process of claim 48 wherein the soft crosslinker is one or more of 2,2-bis(4-methacryloxy-2-ethoxyphenyl) propane, and diethyleneglycol-bis-methacrylate.

51. The process of claim 48 wherein the hard crosslinker is one or more of (i) the adduct of pyromellitic acid dianhydride and 2-hydroxyethylmethacrylate, (ii) the adduct of 3,3',4,4'-benzophenonetetracarboxylic dianhydride and 2-hydroxyethylmethacrylate, (iii) 4-methacryloxytrimellitic anhydride, and (iv) other compounds containing at least one group or moiety capable of free radical polymerization and at least one aromatic ring or moiety containing electron-withdrawing substituents that do not interfere with free radical polymerization.

* * * * *